(12) United States Patent
Boctor et al.

(10) Patent No.: US 7,901,357 B2
(45) Date of Patent: Mar. 8, 2011

(54) ROBOTIC 5-DIMENSIONAL ULTRASOUND

(75) Inventors: Emad M. Boctor, Baltimore, MD (US);
Michael Choti, Glen Arm, MD (US);
Gabor Fichtinger, Bethesda, MD (US);
Russell Taylor, Severna Park, MD (US);
Jerry L. Prince, Lutherville, MD (US)

(73) Assignee: The John Hopkins University, Baltimore, MD (US)

( * ) Notice: Subject to any disclaimer, the term of this patent is extended or adjusted under 35 U.S.C. 154(b) by 943 days.

(21) Appl. No.: 10/895,397

(22) Filed: Jul. 21, 2004

(65) Prior Publication Data

US 2005/0187473 A1 Aug. 25, 2005

Related U.S. Application Data

(60) Provisional application No. 60/488,941, filed on Jul. 21, 2003.

(51) Int. Cl.
*A61B 8/00* (2006.01)
(52) U.S. Cl. ......... 600/443; 600/437; 600/438; 600/442; 901/1; 901/2; 901/14; 901/19; 901/30; 901/50

(58) Field of Classification Search .................. 600/437, 600/438, 442; 901/1–26, 30–47, 50
See application file for complete search history.

(56) References Cited

U.S. PATENT DOCUMENTS

| 5,524,636 | A | * | 6/1996 | Sarvazyan et al. | 600/587 |
| 6,110,114 | A | * | 8/2000 | Nock et al. | 600/443 |
| 2002/0177775 | A1 | * | 11/2002 | Torp et al. | 600/443 |
| 2004/0024311 | A1 | * | 2/2004 | Quaid, III | 600/428 |
| 2004/0111183 | A1 | * | 6/2004 | Sutherland et al. | 700/245 |

* cited by examiner

*Primary Examiner* — Brian Casler
*Assistant Examiner* — James Kish
(74) *Attorney, Agent, or Firm* — Venable LLP; Henry J. Daley

(57) ABSTRACT

A robotic 5D ultrasound system and method, for use in a computer integrated surgical system, wherein 3D ultrasonic image data is integrated over time with strain (i.e., elasticity) image data. By integrating the ultrasound image data and the strain image data, the present invention is capable of accurately identifying a target tissue in surrounding tissue; segmenting, monitoring and tracking the target tissue during the surgical procedure; and facilitating proper planning and execution of the surgical procedure, even where the surgical environment is noisy and the target tissue is isoechoic.

19 Claims, 7 Drawing Sheets

ROBOTIC 5-DIMENSIONAL ULTRASOUND

CROSS-REFERENCE TO RELATED APPLICATIONS

This application claims the benefit of U.S. Provisional Patent Application No. 60/488,941, filed on Jul. 21, 2003, which is hereby incorporated by reference for all purposes as if fully set forth herein.

The research and development effort associated with the subject matter of this patent application was supported by the National Science Foundation under grant no. EEC9731478.

BACKGROUND OF THE INVENTION

1. Field of the Invention

The present invention relates to ultrasound imaging, and more particularly, to robotic 5-dimensional (5D) ultrasound imaging.

2. Discussion of the Related Art

Ultrasound is widely used in the medical community for intervention therapy. Examples include thermal ablation, external beam radiation therapy (EBRT), Brachy therapy, and needle insertion procedures, including biopsy procedures.

As stated, thermal ablation is but one procedure for which ultrasound is commonly used. Primary and metastatic liver cancer represents a significant source of morbidity and mortality in the United States, as well as worldwide. The medical community has focused on such techniques as thermal ablation, and in particular, radiofrequency ablation (RFA), to treat this and other similar diseases. Thermal ablation typically utilizes images to guide the placement of the ablation probe to or within the target area (e.g., a lesion or tumor) of the liver parenchyma. Heat created around the electrode, which is generally located at the tip of the ablation probe, is conducted into the target area tissue, causing coagulative necrosis at a temperature between 50° C. and 100° C.

There are several problems associated with conventional thermal ablation techniques. First and foremost is the ability to effectively utilize the imagery to precisely control the ablation probe during the ablation procedure. To some extent, this problem has been addressed by the development and use of 3D ultrasound imaging systems. While ultrasound is commonly used for target imaging, in general, and ablation monitoring, problems still exist even with these systems, as they do not provide adequate imagery and, as a result, they cannot effectively identify, segment, monitor or track target tissue, nor do they facilitate planning or control prior to and during the ablation process.

One reason conventional robotic 3D ultrasound systems are inadequate is that ultrasound cannot detect all lesions and tumors. Lesions and tumors are may be categorized as either hyperechoic (i.e., appear brighter than the surrounding tissue in an image), hypoechoic (i.e., appear darker than the surrounding tissue in an image), or isoechoic (i.e., have the same intensity as the surrounding tissue in an image). Ultrasound cannot visualize lesions or tumors that are isoechoic. Thus, conventional 3D ultrasound systems cannot effectively identify, segment, monitor or track target tissue, or facilitate planning and control prior to and during an ablation process where the target tissue is isoechoic.

Another reason conventional 3D ultrasound based systems are not always effective is that such systems do not necessarily provide adequate imaging in a noisy environment. As one skilled in the art will appreciate, the operation of an ablation probe generates a significant amount of noise which otherwise interferes with the ultrasound signal, and the ability of the system to generate accurate imagery.

Thermal ablation is, as stated, only one example of a medical procedure for which ultrasound is used to facilitate the procedure. Given the important of ablation therapy, as well as other medical procedures that utilize ultrasound, it is clear there is a tremendous need to enhance the capabilities of imaging systems to overcome the problems described above.

SUMMARY OF THE INVENTION

The present invention involves robotic 5D ultrasound imaging to overcome the various problems associated with conventional 3D ultrasound systems. In general, the present invention achieves this by integrating 3D ultrasound imagery with strain (i.e., elasticity) imagery over time, where strain imagery and time represent a fourth and a fifth degree of freedom, respectively, hence, 5D ultrasound imagery. In addition, the present invention utilizes a robotic end-effector to provide different compression profiles and to provide precise synchronization between the ultrasound acquisition and strain estimation. Still further, the present invention integrates this 5D information and projects it into a 4D visualization over time.

Elasticity imaging is generally known, where elasticity imaging provides a remote and non-invasive representation based on the mechanical properties of the target tissue. These elastic or mechanical properties associated with the target tissue cannot be measured directly. Thus, a mechanical disturbance is applied, and the resulting response is evaluated. One may categorize elasticity imaging into static (i.e., strain based) imaging, dynamic (i.e., wave based) imaging, and mechanical (i.e., stress based) imaging. The strain based approach involves imaging the internal motion if the tissue under static deformation. In contrast, the dynamic approach involves imaging shear wave propagation, and the mechanical approach involves measuring surface stress distribution. Each of these approaches further involve 1) capturing data during externally or internally induced tissue motion or deformation, 2) evaluating tissue response (displacement, strain, or stress), and if needed 3) reconstructing the elastic modulus based on the theory of elasticity.

In accordance with a preferred embodiment of the present invention, the strain based imaging approach is employed. However, one of skill in the art will understand that the use of any one of the other elastic imaging approaches is within the scope and spirit of the present invention.

One advantage of the present invention is that it provides an adequate visualization of the target area, even where the target tissue is isoechoic.

Another advantage of the present invention is that it provides for the accurate identification and segmentation of the target area, such that the boundaries and/or contours of the lesion or tumor can more accurately be distinguished from the surrounding tissue, thereby providing more accurate information based on which the system can more accurately and more effectively plan, monitor, track and control the treatment procedure.

Yet another advantage of the present invention is it provides for different synchronization scenarios to assist in generating strain images at the same rate it acquires the ultrasound image data.

In accordance with a first aspect of the present invention, the aforementioned and other advantages are achieved by a computer integrated surgical system. The system comprises an ultrasound imaging system and a workstation. The workstation, in turn, is configured for receiving ultrasound signals from the ultrasound imaging system, and it includes an elasticity imaging module configured for deriving elasticity related parameters relating to target tissue, an ultrasound module configured for providing ultrasound image data reflecting the anatomical structure of the target tissue, and a volume rendering module configured for integrating the strain distribution information and the ultrasound image data and generating a visualization of the target tissue based on both the strain distribution data and the ultrasound image data.

In accordance with a second aspect of the present invention, the aforementioned and other advantages are achieved by a workstation for use in a computer integrated surgical system. The workstation comprises a strain imaging module configured for deriving strain distribution information relating to target tissue, an ultrasound module configured for providing ultrasound image data reflecting the anatomical structure of the target tissue, and a volume rendering module configured for integrating the strain distribution information and the ultrasound image data and generating a visualization of the target tissue based on both the strain distribution data and the ultrasound image data.

In accordance with a third aspect of the present invention, the aforementioned and other advantages are achieved by a method for rendering an ultrasonic image. The method involves acquiring ultrasound image data of a target tissue and acquiring strain image data of the target tissue. Then, the ultrasound image data and strain image data are integrated and a visualization of the target tissue based on both the ultrasound image data and the strain image data is generated.

In accordance with a fourth aspect of the present invention, the aforementioned and other advantages are achieved by a method of generating segmentation data using ultrasound image data in a medical procedure. The method involves acquiring ultrasound image data of a target tissue, acquiring strain image data of the target tissue, generating a model from the strain image, utilizing the model as an input to a model based segmentation process, and generating segmentation data associated with the target tissue based on the strain image data.

In accordance with a fourth aspect of the present invention, the aforementioned and other advantages are achieved by a method of registering online ultrasound data to preoperative non-ultrasound. The method involves combining tissue/organ boundaries from 3D ultrasound image data, augmenting elasticity to generate a pseudo, non-ultrasound data that can be used to register with preoperative, non-ultrasound data, utilizing a strain component as a landmark to automate a first initial matching registration, utilizing anatomy data to fine-tune the registration, and incorporating anatomy information and elasticity in a registration metric.

It is to be understood that both the foregoing general description and the following detailed description are exemplary and explanatory and are intended to provide further explanation of the invention as set forth in the claims.

BRIEF DESCRIPTION OF THE DRAWINGS

The accompanying drawings together with the description serve to explain the principles of the present invention. In the drawings.

DETAILED DESCRIPTION OF THE ILLUSTRATED EMBODIMENTS

Figure 1:
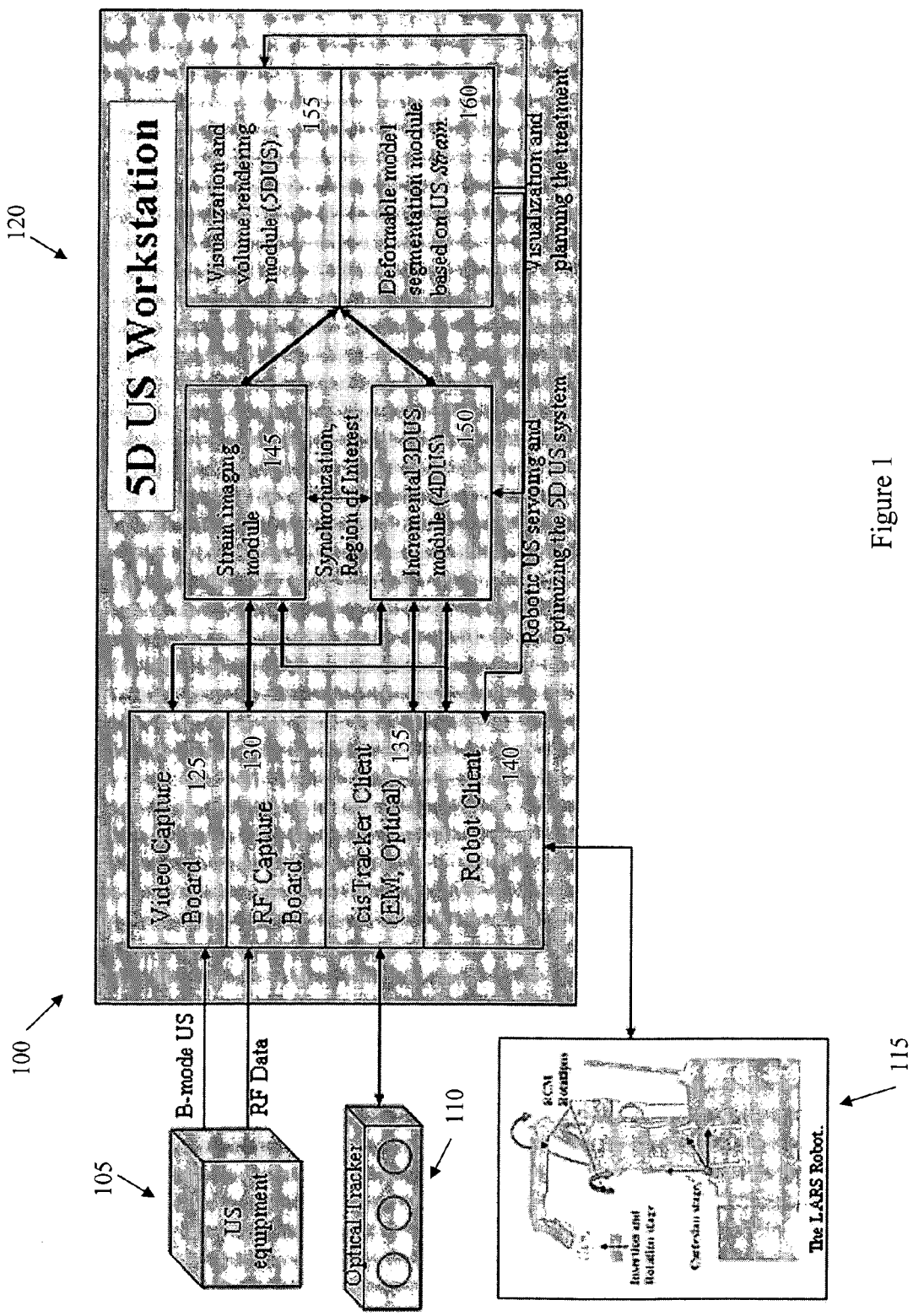
FIG. 1 is a block diagram of a robotic 5D ultrasound system in accordance with exemplary embodiments of the present invention.

The focus of the present invention is a robotic 5D ultrasound system and method for use in the field of Image Guided Therapy (IGT) and, more generally, Computer Integrated Surgery (CIS). The robotic 5D ultrasound system and method, in accordance with exemplary embodiments of the present invention enhance "surgical CAD-CAM-TQM" systems by integrating over time 3D ultrasonic image data with strain (i.e., elasticity) image data.

"Surgical CAD" is analogous to computer-aided design (i.e., CAD) in manufacturing systems, wherein the CAD phase involves the design and/or planning of the intended treatment using an IGT system. In general, prior to such medical procedures, medical images, anatomical atlases and other information are combined for the purpose of generating a model of an individual patient. The model is then used for planning the treatment or intervention procedure. The present invention, however, offers new capabilities with respect to the planning based on more accurate information as a result of integrating elasticity and anatomical variation information simultaneously. More specifically, the present invention uses both elasticity (i.e., strain) image data and ultrasound image data to more accurately identifying the targeted lesions and surrounding critical structures and to more effectively plan optimized therapy patterns (CAD).

The following are examples illustrating some of the ways in which the robotic 5D ultrasound system and method of the present invention facilitate surgical CAD process.

Identifying lesion or tumor boundaries for both isoechoic and non-isoechoic tissue in planning treatment. Ultrasound cannot differentiate isoechoic tumors from surrounding tissue, as the tumor tissue and the surrounding tissue have the same scattering/acoustic signature. Regardless, tumors tend to have different elastic (i.e., mechanical) characteristics compared to normal tissue. The 5D ultrasound system and method of the present invention exploits this difference, and is capable of identifying the tumor through the use of elasticity image data. In non-isoechoic scenarios (i.e., hyperechoic or hypoechoic), ultrasound images often suffer from a data incompleteness problem, due to the tissue boundary not being perpendicular to beam direction. However, once again, the the 5D ultrasound system of the present invention overcomes this problem as image data based on tissue elasticity properties can clearly delineate those boundaries.

Identifying organs and sub-organs from surrounding structure, such as prostate and its lobes. This capability is particularly beneficial in pre-planning EBRT (External Beam Radiation Therapy) treatment or Brachy therapy.

Defining realistic registration algorithms based on elasticity in addition to the anatomical variations. This leads to more accurate statistical atlases and, therefore, more accurate planning at the end.

"Surgical CAM" is analogous to computer-aided manufacturing. In the "surgical CAM" phase, data from the preoperative planning phase (i.e., the images, models, plan geometry, etc.) is made available to the attending technician or physician, for example, in the operating room. Real time image and other sensor data are used to update the information during the course of the procedure. The actual surgical procedure is performed by the surgeon with the assistance of the CIS system. In this surgical CAM phase, the 5D ultrasound system and method, in accordance with the present invention, enhance surgical CAD-CAM-TQM" systems in the following ways.

Segmenting (i.e., defining with particularity the contours of the target lesion or tumor). The 5D ultrasound system and method provides this capability even where the lesion or tumor is isoechoic, as stated above. In addition, the segmentation data is more reliable, as it is based on two reliable sources of information, the anatomy information as well as the elasticity information.

Volume-rendering. The present invention is capable of providing a clear and accurate projection of the 4D image data (i.e., 3D anatomy in addition to elasticity) in real-time. This capability is particularly beneficial for thermal ablation, for example, liver ablation under interaoperative or laparoscopic ultrasound guidance.

Registering online ultrasound data to preoperative non-ultrasound data, such as computer-tomography (CT) data, magnetic resonance imaging (MRI) data and X-ray data. The present invention can achieve this in a more reliable manner through the use of unified elasticity imaging framework. The elasticity component from the 5D ultrasound data can be used to register the ultrasound data to non-ultrasound data in the following ways: 1) by combining the tissue/organ boundaries from the 3D ultrasound image data and augment elasticity to generate a pseudo CT/MRI that can be used to register with non-ultrasound data, 2) using the strain component as a landmark (hard/soft regions) to help automate a first initial matching registration, and continue using anatomy data, and 3) incorporating both anatomy information and elasticity in the registration metric (i.e. energy function, correlation based metrics, mutual information etc. . . . ).

Providing fast and reliable motion tracking. The present invention is capable of providing this based on elasticity and/or speckle correlation. For example, tumors with distinct elasticity parameters can be easily tracked, and undesired motions can then be compensated for.

"Surgical TQM" refers to "total quality management," and it reflects the important role that the a CIS system can play in reducing surgical errors and promoting better, more consistent outcomes. It is always a crucial goal to ensure that the planned therapeutic intervention has in fact been completely and successfully performed before the patient leaves the operating room. In this phase, the assessment process must be integrated with planning and therapy delivery systems to permit interactive re-planning based on this feedback (TQM). The present invention facilitates the TQM phase in a number of ways for a wide variety of clinical/surgical applications.

With respect to ablative procedures, the present invention is capable of identifying the ablation region in 3D and in real-time. Knowing the elasticity of the growing hard necrosis helps define the termination of the procedure, the need for a second intervention, and ablation parameters to be modified according to the delivered monitored therapy.

With respect to needle interventions, the present invention provides an elasticity map of the soft tissue under intervention that could be used to predict future needle deflection and compensate for it.

FIG. 1 is a block diagram of a robotic 5D ultrasound CIS system 100 that is capable of processing RF data, raw 3D ultrasound data and strain image data in interactive or real-time, in accordance with exemplary embodiments of the present invention. As shown, the robotic 5D ultrasound CIS system 100 includes an ultrasound sensor 105, an optical tracker 110, a surgical robot 115 and a 5D ultrasound workstation 120. The 5D ultrasound workstation 120, in turn, contains several components or modules, each of which will now be described in greater detail.

First, the 5D ultrasound workstation 120 includes a video capture board 125. The video capture board 125 receives and processes the B-mode 2D ultrasound video data generated by the ultrasound sensor 105. The video capture board 125 is a standard piece of equipment that may be purchased "of-the-shelf." An example of a suitable video capture board is the MeteorII video processing board made by Matrox Inc. Alternatively, the video capture board 125 could be replaced by a digital video processing board if the ultrasound sensor 105 supported digital link (e.g., DV firewire, optical link etc. . . . ). In another alternative, the B-mode video data can be derived from the raw RF data.

Second, the workstation 120 includes an RF capture board 130. The RF capture board 130 receives and digitizes the raw RF data that corresponds to the 2D ultrasound data generated by the ultrasound sensor 105. The RF capture board 130, like the video capture board 125, is standard, and it can be implemented using almost any high frequency digitizer card, where it would be preferable that the digitizer card is capable of operating at a frequency 10× that of the ultrasound probe operating frequency.

In addition, the workstation 120 includes a CIS tracker module 135. The CIS tracker module 135 receives and processes signals from the optical tracker 110, from which, the position of the ultrasound probe and the robot end-deflector may be determined. A suitable device for the CIS tracker module 135 would be the tracker module developed by ERC CISST Lab.

The workstation 120 further includes a robot client module 140. The robot client module 140 communicates with the robot 115 and, more specifically, provides control commands to the robot 115. The robot client 140 may be the Medical Robot Control (MRC) device developed by the ERC CISST Lab.

The next components in workstation 120 are the strain imaging module 145 and the incremental 3D ultrasound module 150. The strain imaging module 145 generates the strain characteristics of the captured 2D ultrasound data, which can be estimated as quickly as the B-mode acquisition. The strain estimation algorithm may be correlation-based, as shown, for example, in FIG. 3, or information based, as described in greater detail below. The incremental 3D ultrasound module 150 is responsible for reconstructing the 2D ultrasound data into 3D volumes. It interfaces with the video capture board 125, the tracker 135 and the robot client 140. It is referred to here as incremental 3D as it is possible to use a 1D array or an array that produces 2D ultrasound image data, where the probe is moved and the data is acquired incrementally. It is possible to employ a 3D ultrasound probe as well as a 2D array capable of producing 3D ultrasound data in an interactive way. Of particular importance, is the fact that the acquisition of the strain characteristics and the acquisition of the 3D ultrasound data is synchronized, where that synchronization is, at lest in part, controlled by the robot subsystem.

The workstation 120 also includes a 5D visualization and volume rendering module 155. This module provides a volume rendering pipeline that merges both 3D ultrasound anatomy information with elasticity data. The pipeline provides a projection of the 4D data (i.e., 3D anatomy and 1D elasticity) into 3D scenes over time. The projections can be implemented in many ways. In general, however, and in accordance with exemplary embodiments of the present invention, the elasticity data is blended with the anatomy data.

Figure 2:
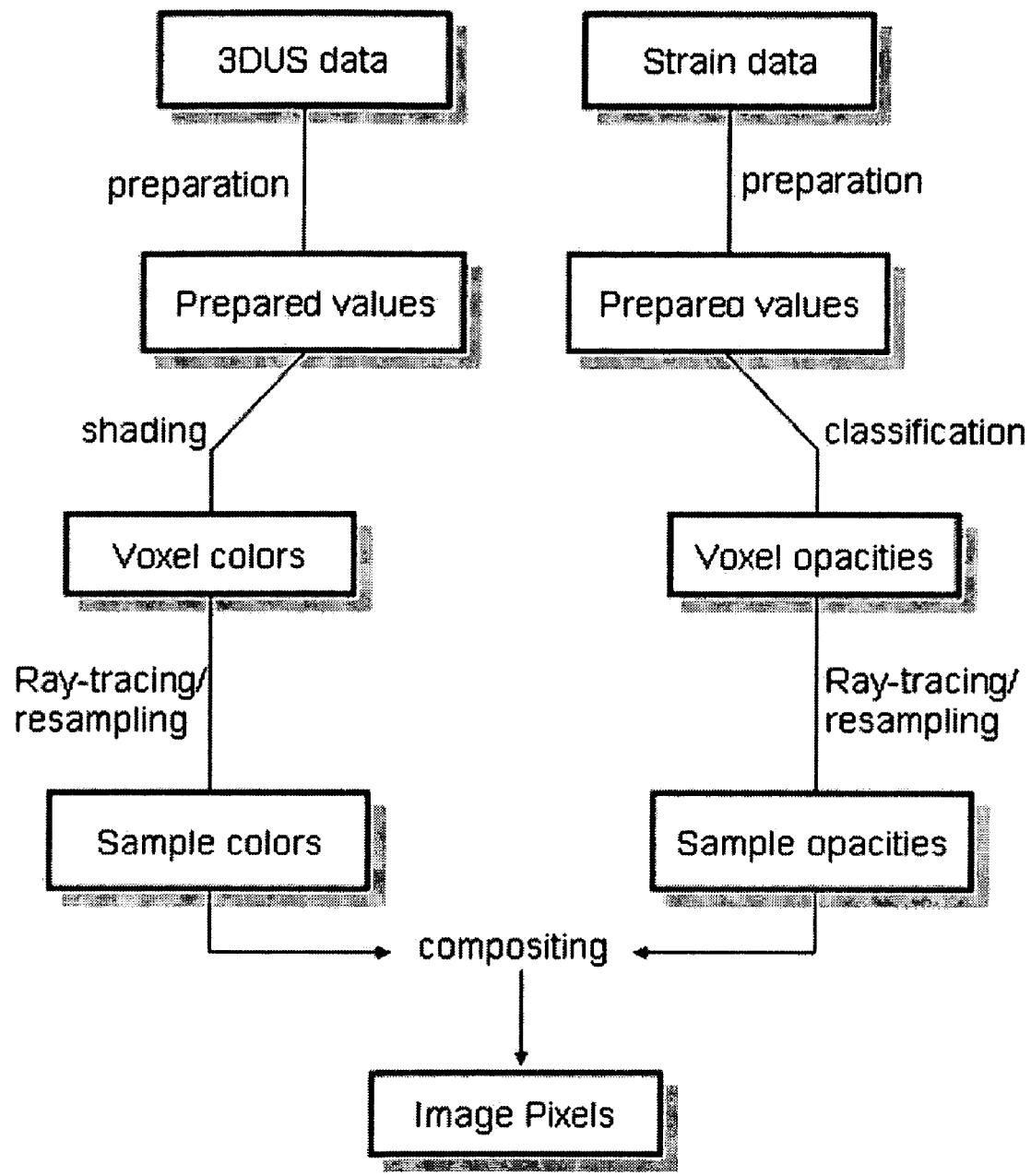
FIG. 2 is a flowchart of a method for rendering a 5D ultrasound based image in accordance with exemplary embodiments of the present invention.

FIG. 2 is a flowchart illustrating an exemplary method for achieving the volume rendering pipeline described above, where elasticity is the controlling parameter. More specifically, FIG. 2 shows a technique for volume rendering ultrasound data with opacity reflecting the strain data. Volume rendering is always a challenge with respect to ultrasound data. However, using elasticity data makes it possible to generate a more useful and more meaningful 3D image where, for example, the boundaries appear in a non-uniform way due to the change in angle between the boundary points and the ultrasound beam direction. Such images are particularly meaningful in IGT and CIS applications. It should be noted that volume rendering can easily be carried out in real-time using a volume rendering card, such as the Volume Pro 1000, made by Terarecon Inc.

Finally, the workstation 120 includes the deformable model segmentation module 160. As stated, the present invention provides a useful tool for IGT and CIS applications. One main challenge in this field is to have a reliable real-time tracking mechanism. This is easily with the present invention for a wide variety of surgical interventions due to the integration of elasticity information, as well as the use of feedback data and control which is generally provided by the segmentation module 160, as shown in FIG. 1.

Figure 3:
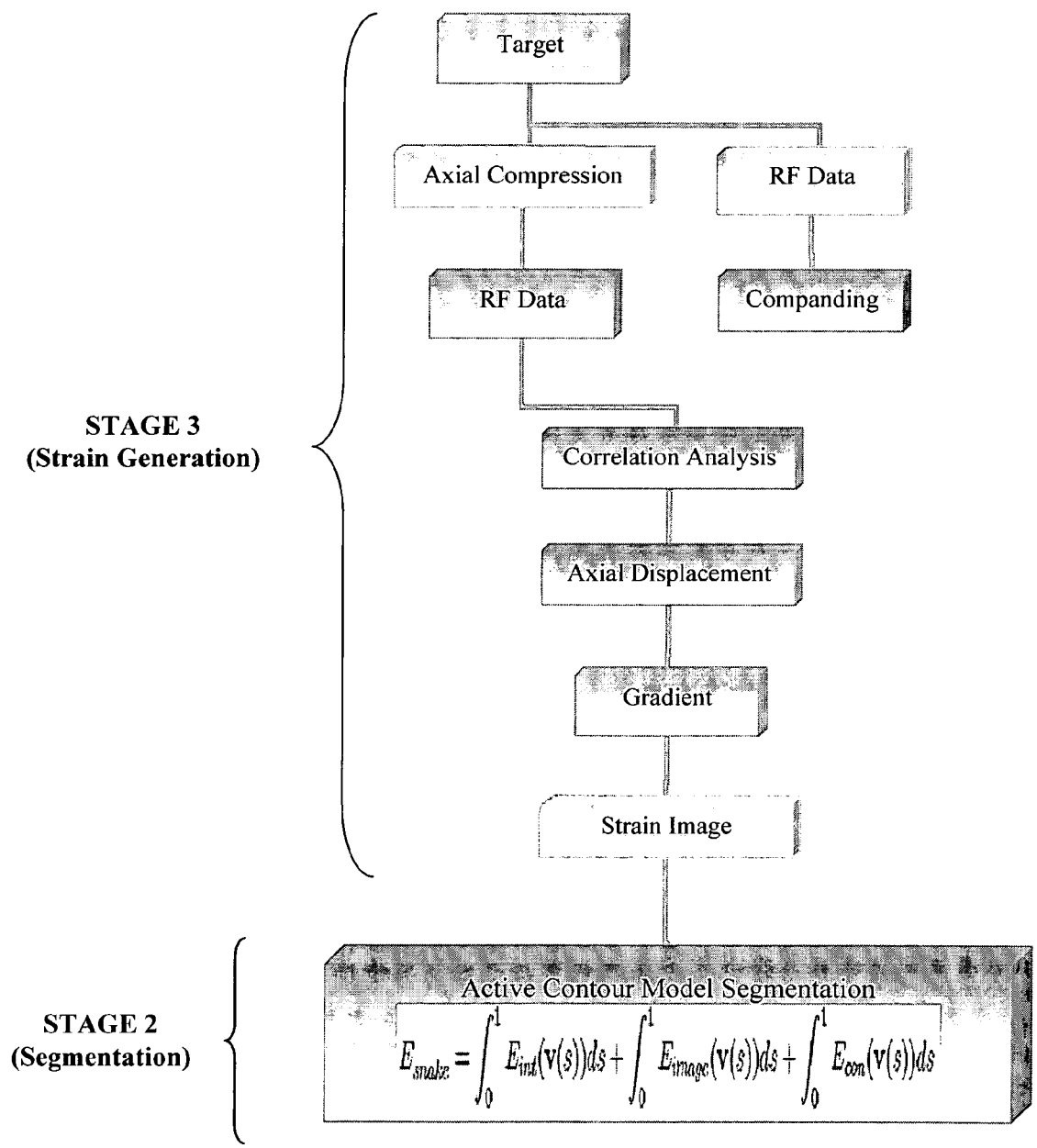
FIG. 3 is a flow chart of a method for providing segmentation based on ultrasound and strain image information, in accordance with exemplary embodiments of the present invention.

Referring now to FIG. 3, this flow diagram illustrates an implementation for achieving strain imaging estimation. In general, the implementation illustrated in FIG. 3 comprises two main stages. The first stage involves normal strain generation, in accordance with a correlation based technique. This is followed by stage two, which involves a model based segmentation technique. More specifically, the implementation starts with the acquisition of two frames, each having different compression states, followed by companding (i.e., signal processing preconditioning) to compensate for the compression. This results in better correlation. Next, a correlation technique (i.e., Normalized Cross-Correlation, SSD, SAD, Mutual Information, etc. . . . ). From the estimated motion, we can get the strain by getting the gradient according to continuum mechanics.

With regard to the Phase 2 in FIG. 3, elasticity data can be used, for a wide variety of clinical applications, to provide a first approximation for model based segmentation. This is not a trivial task with conventional systems, particularly where the target tissue is isoechoic, as explained above. In many conventional systems, this first approximation is simply a best guess that is provided by the physician. Here the first approximation is automatically and accurately generated as a function of the elasticity data. In Phase 2 of FIG. 3, the segmentation process is implemented using the basic energy formula for 2D "snake model." However, one of skill in the art will understand that this could be extended to 3D, or that implementation may be achieved using any model based segmentation technique.

As stated above, the strain estimation may be correlation based, as set forth, for example, in the first stage of the process illustrated in FIG. 3. Alternatively, the strain estimation may be derived using an information based technique as described herein below.

Estimating the local strain is an essential step, which requires a high level of accuracy, since the amplitude of tissue deformation is relatively small. In accordance with exemplary embodiments of the present invention, two techniques are primarily considered. The first technique utilizes the maximization of normalized cross-correlation between the pre- and post-compression RF signal after applying ID companding. This is illustrated in FIG. 3. This is considered a primitive delay estimation algorithms that is implemented in time-domain. Most advanced time delay estimation algorithms are implemented in frequency-domain; for example the generalized cross-correlation method. The spectral estimation in case of short signal segments is the most important weakness of the frequency-domain implementations. Others have searched for a time-domain implementation of an advanced delay estimation algorithm, and in doing so, found the "information theoretic delay criterion". A detailed description of the information based algorithm is set forth in R. Moddemeijer, *Delay-Estimation with Application to Electroencephalograms in Epilepsy*, Universiteit Twente, 1989, Enschede (NL), ISBN: 90:9002668-1, the contents of which are incorporated herein by reference.

As stated above, and as illustrated in FIG. 1, the CIS system 100 includes a medical robot 115. The robot 115 is an important component as it provides several different yet important functions, such as controlling the rapid and frequent capture of pre and post compression ultrasound data, as well as synchronizing ultrasound scanning and compression so that it is possible to acquire rapid, accurate and synchronized strain and 3D ultrasound data. FIGS. 4-7 illustrate exemplary configurations associated with the robot 115, and the aforementioned functions provided the robot 115.

Figure 4:
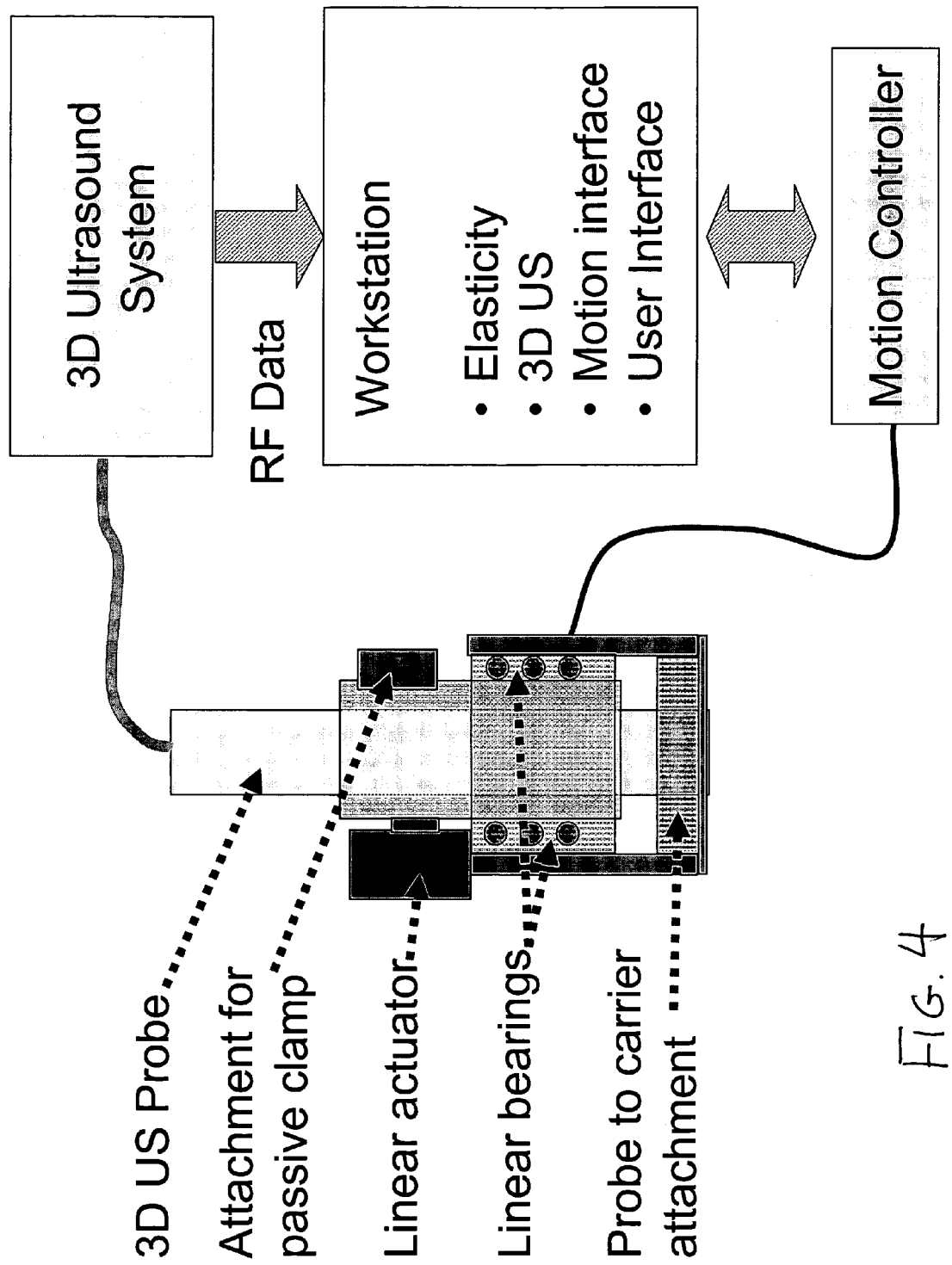
FIGS. 4-7 illustrate exemplary configurations associated with the medical robot, in accordance with exemplary embodiments of the present invention.

FIG. 4, for example, shows the configuration of a robotic end-effector 400 which comprises, among other things, using linear actuators 402 and a compression plate 404. The linear actuators 402 and the compression plate 404 move along an axial path in the direction of the ultrasound beam, where the ultrasound probe 405 is either rotated or translated within the volume. In accordance with the present invention, a 3D ultrasound probe can be fixed, where only the compression plate moves. Alternatively, the probe may be rotated to acquire multiple 3D ultrasound data sets for the same volume of interest using different lateral and elevation resolutions. This can, with careful compounding, enhance the signal-to-noise ratio and, in turn, enhance the 5D ultrasound data. In general, the motion scenarios can be either a) moving one part (i.e., either the ultrasound probe or the compression plate) or b) moving both the probe and the compression plate at the same time. Scenario "a" basically starts by moving the compression plate and then acquiring the 3D ultrasound data. The compression plate is then moved and 3D ultrasound data is once again acquired. If a strain image is generated from "n" compressions, the strain rate will be the rate of the 3D ultrasound acquisition divided by "n". Scenario "b" involves linearly moving the plate and rotating the ultrasound probe at the same time. This means that every two consecutive images will have different compression levels.

Figure 5:
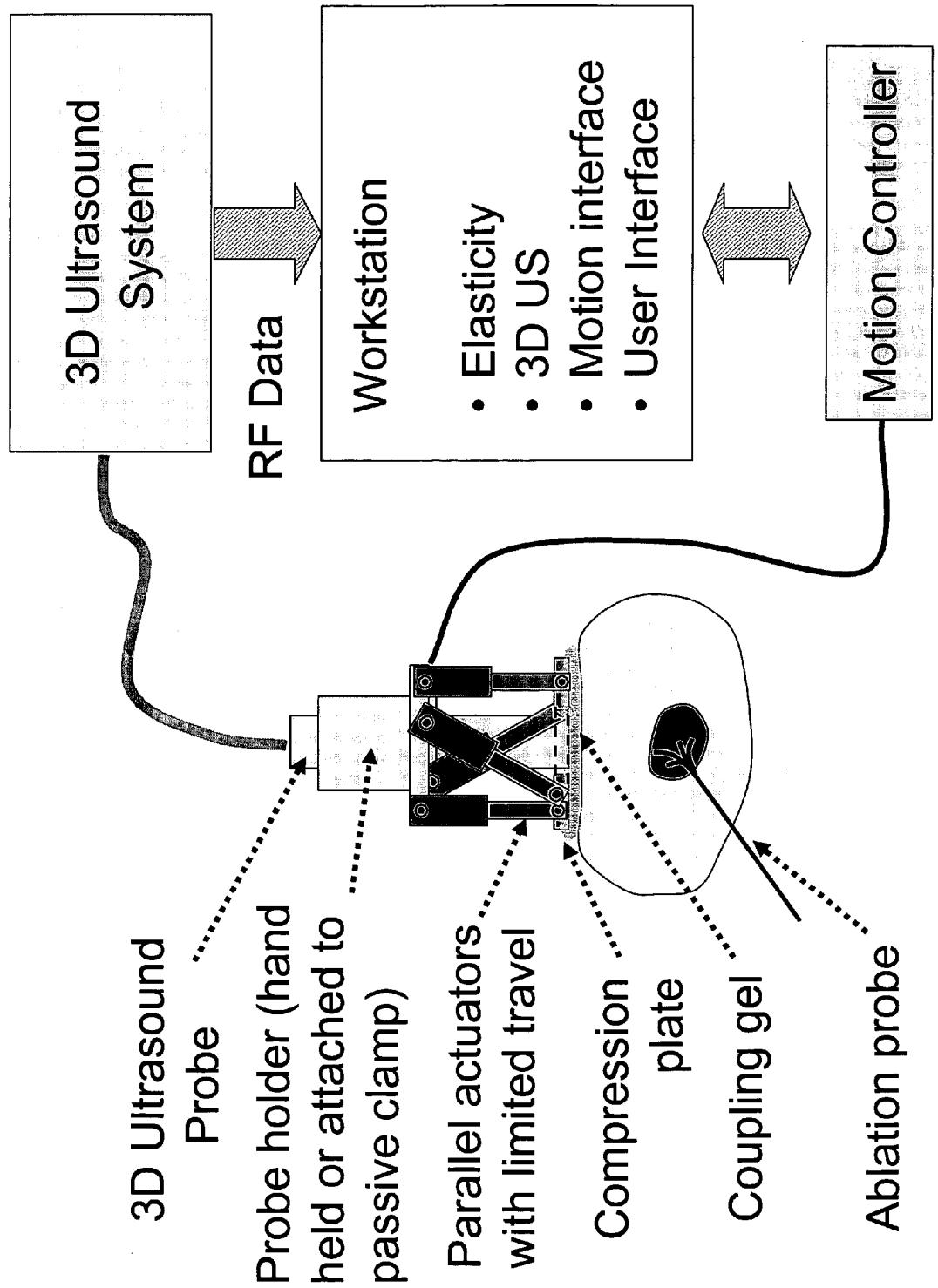
Figure 6:
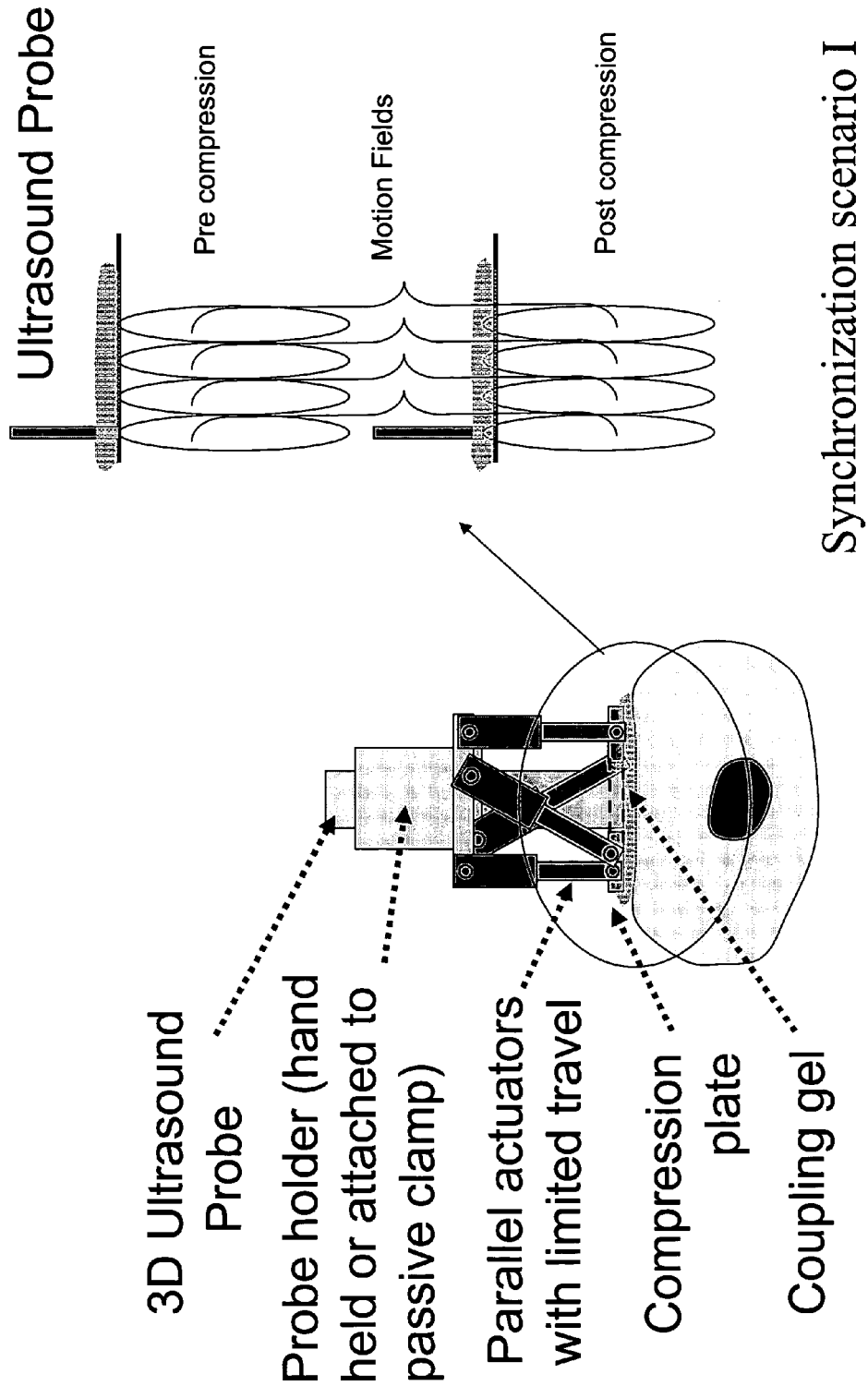
Figure 7:
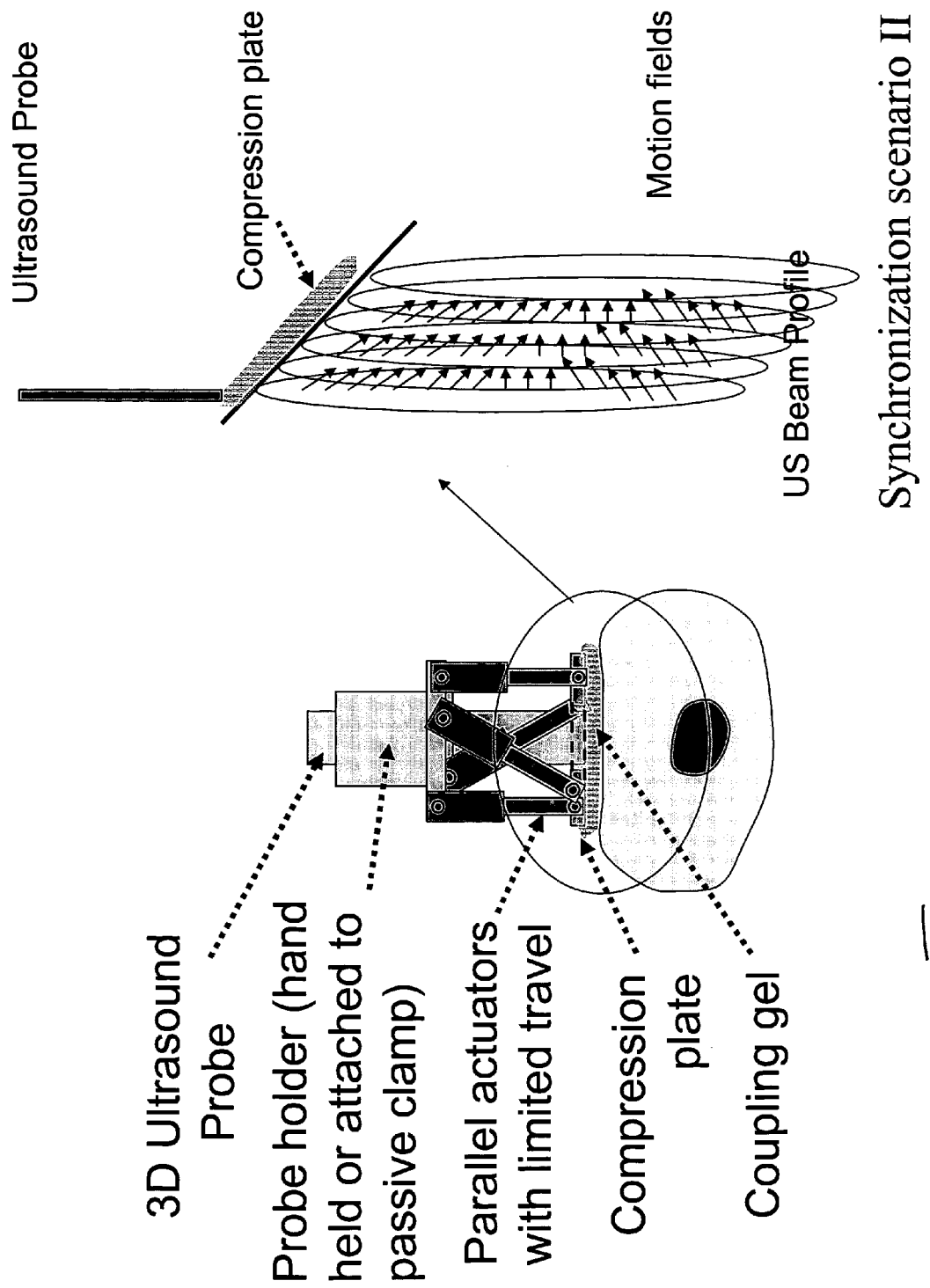

FIG. 5 shows a more preferable design, also capable of delivering a high rate of strain. Here, the end-effector is based on a multi-parallel actuator design. The same motion scenarios described above, also apply here, as FIG. 6. FIG. 7 shows that it is possible to compress the tissue obliquely while moving the 2D ultrasound probe. This means that every two consecutive ultrasound beam profiles will have a different compression level, thus, strain rate can be generated at the same 3D ultrasound volume acquisition rate. Moreover, it is no longer necessary to adjust the compression rate to accommodate tissue response. This results in a more reliable motion profile and greater accuracy. Additionally, the same volume under a different pressure profile can lead to better strain compounded volume.

It will be apparent to those skilled in the art that various modifications and variation can be made in the present invention without departing from the spirit or scope of the invention. Thus, it is intended that the present invention cover the modifications and variations of this invention provided they come within the scope of the appended claims and their equivalents.

What is claimed is:

1. A computer integrated surgical system comprising:
    an ultrasound imaging system;
    a medical robot; and
    a workstation configured to receive ultrasound signals from the ultrasound imaging system and control the medical robot, said workstation comprising:
        a strain imaging module configured to compute strain distribution data corresponding to ultrasound imaging system signals and medical robot signals, wherein the strain imaging module computes the strain distribution data at a strain data frame rate;
        an ultrasound module configured to provide ultrasound image data reflecting the anatomical structure of the target tissue, wherein the ultrasound module provides the ultrasound image data at an ultrasound image data frame rate; and
        a volume rendering module configured to generate a visualization of target tissue based on a function of said strain distribution data and said ultrasound image data,
    wherein said function differentiates said target tissue from surrounding tissue.

2. The system of claim 1, wherein the medical robot comprises an end-effector.

3. The system of claim 2, wherein the end-effector comprises a linear actuator.

4. The system of claim 2, wherein the end-effector comprises parallel actuators.

5. The system of claim 2, wherein the medical robot further comprises means for synchronizing the acquisition of ultrasound image data and strain distribution data.

6. The system of claim 2, wherein the medical robot is configured to compress the target tissue and induce a strain distribution.

7. The system of claim 2, wherein the end-effector comprises:
    a linear actuator, a compression plate, and a ultrasound probe, the ultrasound probe configured to move linearly and the ultrasound probe configured to rotate while linearly moving the compression plate.

8. The system of claim 2, wherein the end-effector comprises:
    a means for creating an ultrasound image having a first compression level and a second compression level for every two consecutive ultrasound images.

9. The system of claim 1, further comprising a segmentation module configured to provide feedback segmentation data to a medical robot client module, wherein the medical robot client module comprises means for generating medical robot signals to cause mechanical motion of the medical robot as a function of the feedback data provided by the segmentation module.

10. The system of claim 9, wherein the segmentation module is further configured to provide feedback segmentation data to the volume rendering module.

11. The system of claim 1, wherein each pixel of said visualization generated by said volume rendering module has a first pixel parameter determined by at least one of a corresponding strain value or a corresponding ultrasound image value and a second pixel parameter determined by at least one of a corresponding strain value or a corresponding ultrasound image value.

12. The system of claim 11, wherein said first pixel parameter is color and said second pixel parameter is opacity.

13. The system of claim 1, further comprising an elasticity imaging module configured to derive elasticity related parameters relating to the target tissue.

14. The system of claim 13, wherein the elasticity imaging module can be reconfigured to estimate elasticity parameters based on strain based static imaging, wave based dynamic imaging and stress based mechanical imaging.

15. A workstation, configured to be coupled to an ultrasound imaging system and a medical robot, for use in a computer integrated surgical system, said workstation comprising:
    a medical robot client module configured to receive ultrasound data from the ultrasound imaging system at an ultrasound data acquisition rate, and to receive strain data resulting from mechanical motion of the medical robot at a strain data acquisition rate, wherein the ultrasound data acquisition rate and the strain data acquisition rate are substantially equal;
    a strain imaging module configured to derive strain distribution data relating to target tissue motion or deformation resulting from mechanical motion of the medical robot;
    an ultrasound module configured to provide ultrasound image data reflecting the anatomical structure of the target tissue; and
    a volume rendering module configured to generate a visualization of target tissue based on a function of said strain distribution data and said ultrasound image data,
    wherein said function differentiates said target tissue from surrounding tissue.

16. The workstation of claim 15, further comprising a segmentation module configured to provide feedback segmentation data to the medical robot client module, wherein the medical robot client module comprises means for generating medical robot control signals to cause mechanical motion of the medical robot as a function of the feedback data provided by the segmentation module.

17. The workstation of claim 16, wherein the segmentation module is further configured to provide feedback segmentation data to the volume rendering module.

18. The workstation of claim 15, wherein each pixel of said visualization generated by said volume rendering module has a first pixel parameter determined by at least one of a corresponding strain value or a corresponding ultrasound image value and a second pixel parameter determined by at least one of a corresponding strain value or a corresponding ultrasound image value.

19. The workstation of claim 18, wherein said first pixel parameter is color and said second pixel parameter is opacity.

* * * * *

UNITED STATES PATENT AND TRADEMARK OFFICE
CERTIFICATE OF CORRECTION

| | | |
|---|---|---|
| PATENT NO. | : 7,901,357 B2 | Page 1 of 1 |
| APPLICATION NO. | : 10/895397 | |
| DATED | : March 8, 2011 | |
| INVENTOR(S) | : Boctor et al. | |

It is certified that error appears in the above-identified patent and that said Letters Patent is hereby corrected as shown below:

On the Title Page

Item (73) Assignee: should read,

** The John*s* Hopkins University **

Signed and Sealed this
Twenty-sixth Day of April, 2011

David J. Kappos
*Director of the United States Patent and Trademark Office*